US009198271B2

(12) United States Patent
Miyachi

(10) Patent No.: US 9,198,271 B2
(45) Date of Patent: Nov. 24, 2015

(54) X-RAY IMAGING APPARATUS, CONTROL DEVICE, RADIATION IMAGING APPARATUS, AND METHOD OF CONTROLLING THE SAME

(71) Applicant: CANON KABUSHIKI KAISHA, Tokyo (JP)

(72) Inventor: Norihiko Miyachi, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 143 days.

(21) Appl. No.: 13/752,466

(22) Filed: Jan. 29, 2013

(65) Prior Publication Data

US 2013/0230141 A1    Sep. 5, 2013

(30) Foreign Application Priority Data

Mar. 2, 2012    (JP) ................. 2012-047302

(51) Int. Cl.
| | |
|---|---|
| *H05G 1/60* | (2006.01) |
| *H04N 5/38* | (2006.01) |
| *G06T 11/00* | (2006.01) |
| *H05G 1/30* | (2006.01) |
| *G01N 23/04* | (2006.01) |
| *H04N 5/321* | (2006.01) |
| *A61B 6/00* | (2006.01) |
| *G06T 1/00* | (2006.01) |
| *H05G 1/00* | (2006.01) |

(Continued)

(52) U.S. Cl.
CPC .. *H05G 1/30* (2013.01); *A61B 6/00* (2013.01); *A61B 6/563* (2013.01); *G01N 23/04* (2013.01); *G06T 11/003* (2013.01); *H04N 5/321* (2013.01); *H04N 5/38* (2013.01); *H05G 1/60* (2013.01); *A61B 6/54* (2013.01); *G06T 1/0007* (2013.01); *H04N 5/32* (2013.01); *H05G 1/00* (2013.01); *H05G 1/08* (2013.01)

(58) Field of Classification Search
CPC ...... A61B 6/52; A61B 6/5205; A61B 6/5211; A61B 6/56; A61B 6/563; A61B 6/566; G01N 23/04; G06F 3/14; H04L 1/1809; H04L 1/1816; H04L 1/1819; H05G 1/00; H05G 1/08; H05G 1/60; H04N 5/32; H04N 5/321; H04N 5/38; G06T 1/0007; G06T 11/003; G06T 2211/40
USPC ........ 378/62, 91, 96, 98, 98.8, 204, 210, 901; 250/370.01, 370.08, 370.09, 371
See application file for complete search history.

(56) References Cited

U.S. PATENT DOCUMENTS

| | | | | |
|---|---|---|---|---|
| 5,719,883 | A  * | 2/1998 | Ayanoglu | 714/751 |
| 6,621,799 | B1 * | 9/2003 | Kemp et al. | 370/282 |
| 7,239,685 | B2 * | 7/2007 | Petrick et al. | 378/116 |

(Continued)

FOREIGN PATENT DOCUMENTS

| | | |
|---|---|---|
| JP | 2005-253783 | 9/2005 |
| JP | 2008-154893 | 7/2008 |

(Continued)

*Primary Examiner* — Anastasia Midkiff
(74) *Attorney, Agent, or Firm* — Fitzpatrick, Cella, Harper & Scinto

(57) ABSTRACT

In transfer of image data (such as an X-ray image), if for example a transfer error occurs, a retransmission timeout time limit for an item of image data that is to be transferred last, in a time sequence of image data transfer, is set to be different from a retransmission timeout time limit for at least one other item of image data which is to be transferred.

18 Claims, 10 Drawing Sheets

(51) Int. Cl.
*H04N 5/32* (2006.01)
*H05G 1/08* (2006.01)

(56) References Cited

U.S. PATENT DOCUMENTS

| | | | |
|---|---|---|---|
| 7,466,345 B2 | 12/2008 | Kameshima et al. | 348/220.1 |
| 8,229,063 B2 | 7/2012 | Nishii | 378/44 |
| 2002/0038441 A1* | 3/2002 | Eguchi et al. | 714/748 |
| 2006/0250949 A1* | 11/2006 | Ramakrishnan et al. | 370/216 |
| 2006/0251010 A1* | 11/2006 | Ramakrishnan et al. | 370/328 |
| 2009/0272909 A1 | 11/2009 | Takenaka et al. | 250/370.09 |

FOREIGN PATENT DOCUMENTS

| | | |
|---|---|---|
| JP | 2009-272673 | 11/2009 |
| JP | 2010-088027 | 4/2010 |

\* cited by examiner

FIG. 7

◆ MOVING IMAGE CAPTURING ⇒ STILL IMAGE CAPTURING
(RETRANSMISSION TIME AT TIME OF MODE SWITCHING IS CHANGED)

X-RAY IMAGING APPARATUS, CONTROL DEVICE, RADIATION IMAGING APPARATUS, AND METHOD OF CONTROLLING THE SAME

BACKGROUND OF THE INVENTION

1. Field of the Invention

The present invention relates to an X-ray imaging technique.

2. Description of the Related Art

Recently, there has been developed a flat panel detector which can perform not only still image capturing but also moving image capturing (Japanese Patent Laid-Open No. 2005-253783). With recent advances in the digitalization of X-ray imaging apparatuses, there is being constructed a full digital system ranging from imaging operation to display operation. Such full digital systems sometimes use a packet communication network for the compact, versatile, and wireless configuration of transmission lines.

When using a packet communication network, the system uses a protocol designed to reliably perform retransmission such as TCP (Transmission Control Protocol) in order to reliably transmit data to a display control device. It is however difficult to increase a data rate for retransmission handling. TCP is one of several standard protocols for the Internet which are designed to perform retransmission at the time of data loss by forming a reliable connection between transmission and reception host processes. This protocol is high in reliability but low in transfer efficiency. In some cases, large packet arrival delays make it impossible to meet a request to display in real time.

For this reason, in order to reduce delays, the UDP (User Datagram Protocol) is used. However, since UDP generates no connection and performs no acknowledgment, there is a risk of packet loss, even through it is possible to implement high-speed transmission. UDP is a standard protocol for the Internet which is designed to perform connectionless communication for only transmission/reception of data between applications, and leaves reliability to the applications themselves. This protocol is low in reliability but high in transfer efficiency. As a method of solving this problem, RTP (Real-Time Transmission Protocol) in an upper UDP layer is known.

In data transmission/reception using the above communication method, packet loss sometimes occurs. As a method of solving this problem, a packet data retransmission method is available (Japanese Patent Laid-Open No. 2010-088027).

Recent X-ray imaging apparatuses have a function of holding the last image made in a previous fluoroscopy if there is an interruption or break in the fluoroscopy, and continuing to display the image on a monitor (Japanese Patent Laid-Open No. 2008-154893).

When switching from the moving image capturing mode to the still image capturing mode, the apparatus holds the last image made in the immediately preceding imaging mode. The last image at this time continues to be displayed until the execution of the next imaging operation, and hence is desired not to have much image data loss. For this reason, the apparatus prevents data loss as much as possible by taking a sufficient time for retransfer using a retransfer function.

When the user checks the state of an object in moving image capturing operation and performs still image capturing at an arbitrary timing to store an image, a retransmission time 400 for the last image is generated, as shown in FIG. 4. This may cause a delay corresponding to the retransmission time in imaging operation relative to the desired timing of still image capturing, resulting in a failure to acquire an arbitrary image.

SUMMARY OF THE INVENTION

The present invention has been made in consideration of the above problem, and provides a technique for, when retransfer occurs due to an image data transfer failure at the time of switching between imaging modes, reducing a delay in switching between the imaging modes due to the retransfer.

According to one aspect of the present invention, there is provided a control device which performs radiation imaging by controlling a digital radiation imaging apparatus, the device comprising: a detection unit which detects an imaging instruction in a specific imaging mode; a transferring unit which transfers outside radiation image data obtained by the digital radiation imaging; a control unit which executes retransmission processing within a retransmission timeout time when the transfer fails; and a setting unit which sets, for image data being transferred last of a plurality of image data captured in a first imaging mode, a retransmission timeout time different from a retransmission timeout time for at least one other item of image data to be transferred.

According to another aspect of the present invention, there is provided a method of controlling a control device which performs radiation imaging by controlling a digital radiation imaging apparatus, the method comprising: a detection step of detecting an imaging instruction in a specific imaging mode; a transferring step of transferring outside radiation image data obtained by the digital radiation imaging; a control step of executing retransmission processing within a retransmission timeout time when the transfer fails; and a setting step of setting, for image data being transferred last of a plurality of image data captured in a first imaging mode, a retransmission timeout time different from a retransmission timeout time for at least one other item of image data to be transferred.

According to still another aspect of the present invention, there is provided an X-ray imaging apparatus comprising: an X-ray generating unit which irradiates an object with X-rays; an X-ray image generating unit which detects X-rays transmitted through the object and generates an X-ray image of the object based on the detected X-rays; and a control unit which acquires the X-ray image from the X-ray image generating unit and transfers the X-ray image to a functional unit which processes the X-ray image, wherein the control unit retransmits, to the functional unit, one X-ray image captured by the X-ray generating unit and the X-ray image generating unit within a preset retransmission time, when a retransmission request for the X-ray image is received from the functional unit after the X-ray image is transferred to the functional unit, sets, as the retransmission time, a period up to the start of capturing the next X-ray image after the transfer, when a moving image mode for capturing a plurality of X-ray images by continuously capturing X-ray images is set, and sets a predetermined time as the retransmission time when a still image mode for capturing one X-ray image is set.

According to yet another aspect of the present invention, there is provided a radiation imaging apparatus comprising: a radiation detector which obtains an image signal by detecting radiation; an output unit which outputs radiation image data based on the image signal to an external device; a control unit which makes the output unit start re-outputting at least part of the radiation image data in accordance with a first signal from an external device, and receives a second signal from the external device or continues the re-outputting until elapse of a specific time from a start of the re-outputting, and a setting unit which sets the specific time based on a second imaging mode executed next to a first imaging mode of radiation imaging for obtaining the image signal.

According to still yet another aspect of the present invention, there is provided a control device comprising: a reception unit which receives image data from a radiation detector; a transmission unit which transmits, to the radiation detector, a signal for requesting retransmission of the image data and a signal indicating a retransmission time for interrupting retransmission of the image data before completion of the retransmission; and a setting unit which sets the retransmission time based on selection of a first imaging mode of radiation imaging for obtaining the image data and a second imaging mode executed sequentially after the first imaging mode.

According to yet still another aspect of the present invention, there is provided a method of controlling an X-ray imaging apparatus including an X-ray generating unit which irradiates an object with X-rays, an X-ray image generating unit which detects X-rays transmitted through the object and generates an X-ray image of the object based on the detected X-rays, and a control unit which acquires the X-ray image from the X-ray image generating unit and transfers the X-ray image to a functional unit which processes the X-ray image, wherein the control unit retransmits, to the functional unit, one X-ray image captured by the X-ray generating unit and the X-ray image generating unit within a preset retransmission time, when a retransmission request for the X-ray image is received from the functional unit after the X-ray image is transferred to the functional unit, sets, as the retransmission time, a period until a start of capturing of a next X-ray image after the transfer, when a moving image mode for capturing a plurality of X-ray images by continuously capturing X-ray images is set, and sets a predetermined time as the retransmission time when a still image mode for capturing one X-ray image is set.

According to still yet another aspect of the present invention, there is provided a method of controlling a radiation imaging apparatus including a radiation detector which obtains an image signal by detecting radiation, the method comprising: an output step of outputting radiation image data based on the image signal to an external device; a control step of starting in the output step re-outputting at least part of the radiation image data in accordance with a first signal from an external device, and receiving a second signal from the external device or continuing the re-outputting until elapse of a specific time from a start of the re-outputting, and a setting step of setting the specific time based on selection of a second imaging mode executed sequentially after a first imaging mode of radiation imaging for obtaining the image signal.

According to yet still another aspect of the present invention, there is provided a method of controlling a control device, the method comprising: a reception step of receiving image data from a radiation detector; a transmission step of transmitting, to the radiation detector, a signal for requesting retransmission of the image data and a signal indicating a retransmission time for interrupting retransmission of the image data before completion of the retransmission; and a setting step of setting the retransmission time based on selection of a first imaging mode of radiation imaging for obtaining the image data and a second imaging mode executed sequentially after the first imaging mode.

Further features of the present invention will become apparent from the following description of exemplary embodiments with reference to the attached drawings.

BRIEF DESCRIPTION OF THE DRAWINGS

FIG. 7 is a view for explaining the operation of the X-ray imaging apparatus 818;

DESCRIPTION OF THE EMBODIMENTS

The embodiments of the present invention will be described below with reference to the accompanying drawings. Note that each embodiment described below shows an example of concrete execution of the present invention, and is one of the specific embodiments of the arrangements described in the scope of the following claims.

First Embodiment

Figure 8:
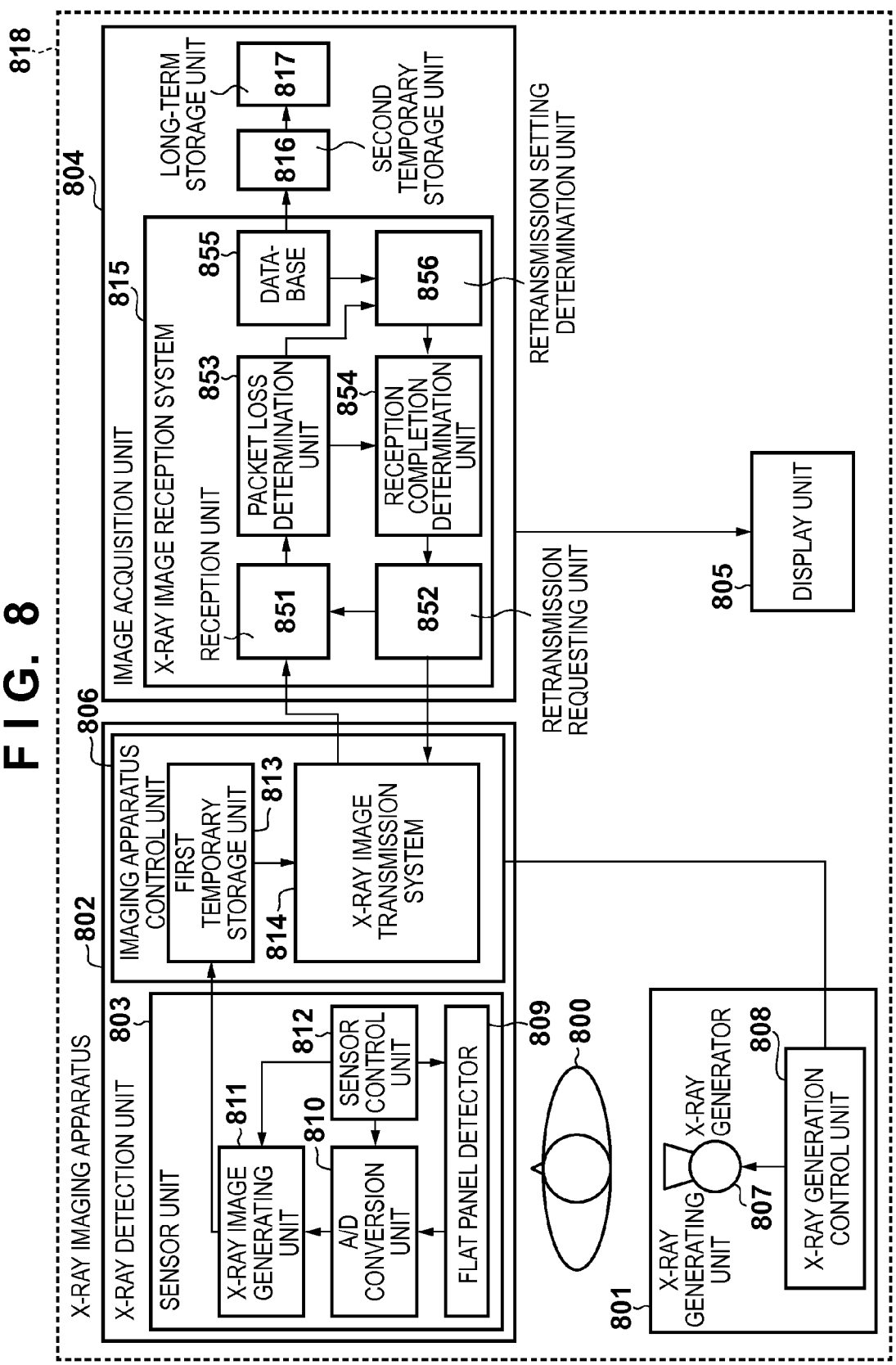
FIG. 8 is a block diagram showing an example of the arrangement of the X-ray imaging apparatus.

An example of the arrangement of an X-ray imaging apparatus which is an example of a radiation imaging apparatus according to this embodiment will be described first with reference to the block diagram of FIG. 8. An X-ray imaging apparatus 818 shown in FIG. 8 is roughly constituted by an X-ray generating unit 801, an X-ray detection unit 802, an image acquisition unit 804, and a display unit 805.

<X-Ray Generating Unit 801>

The X-ray generating unit 801 will be described first. The X-ray generating unit 801 is a unit which irradiates (exposes) an object 800 with X-rays, and includes an X-ray generator (X-ray generating unit) 807, and an X-ray generation control unit 808.

The X-ray generator 807 includes an X-ray tube and emits X-rays. The X-ray generation control unit 808 controls the operation of the X-ray generator 807, and issues instructions to start and stop emitting X-rays to the X-ray generator 807. Upon receiving an X-ray emission enabling signal from an imaging apparatus control unit 806 in the X-ray detection unit 802 as a radiation detector, the X-ray generation control unit 808 performs various preparation processes associated with X-ray emission. Upon completion of these preparation processes, the X-ray generation control unit 808 issues an instruction to start emitting X-rays to the X-ray generator 807. Upon receiving this instruction to start emitting X-rays, the X-ray generator 807 starts irradiating the object 800 with X-rays.

<X-Ray Detection Unit 802>

The X-ray detection unit 802 will be described next. The X-ray detection unit 802 is a unit which generates an X-ray image of the object 800 based on the X-rays transmitted through the object 800, and transfers the generated X-ray image to an X-ray image reception system 815. The X-ray detection unit 802 includes a sensor unit 803 and the imaging apparatus control unit 806.

The sensor unit 803 will be described first. The sensor unit 803 is a unit which detects the X-rays transmitted through the object 800, and generates an X-ray image of the object 800 based on the detected X-rays. This unit includes a flat panel detector 809, a sensor control unit 812, an A/D conversion unit 810, and an X-ray image generating unit 811.

The flat panel detector 809 detects the X-rays transmitted through the object 800 via a two-dimensional X-ray detection surface, accumulates electric charges corresponding to the detected X-ray dose, and then outputs an image signal corresponding to the accumulated electric charges to the A/D conversion unit 810.

The A/D conversion unit 810 converts the signal (analog signal) received from the flat panel detector 809 into a digital signal, and sends the converted digital signal to the X-ray image generating unit 811.

The X-ray image generating unit 811 performs various image processing such as gain correction for the digital signal received from the A/D conversion unit 810, and generates an X-ray image based on the digital signal having undergone the image processing. The X-ray image generating unit 811 transfers the generated X-ray image to the imaging apparatus control unit 806.

The sensor control unit 812 performs operation control for the sensor unit 803, for example, control on the signal acquisition timing of the flat panel detector 809, operation control for the A/D conversion unit 810, and control on the transfer of an X-ray image from the X-ray image generating unit 811 to the imaging apparatus control unit 806.

The imaging apparatus control unit 806 will be described next. The imaging apparatus control unit 806 transfers, to the image acquisition unit 804, the X-ray image transferred from the sensor unit 803, sets an imaging mode (to be described later), and controls the timing of the transmission of an X-ray emission enabling signal to the X-ray generation control unit 808. The imaging apparatus control unit 806 includes a first temporary storage unit 813 and an X-ray image transmission system 814.

The first temporary storage unit 813 is a memory for temporarily storing the X-ray image transferred from the sensor unit 803. Note that the first temporary storage unit 813 may be provided in the X-ray image transmission system 814.

The X-ray image transmission system 814 functions as an output unit which transmits X-ray image data as radiation image data stored in the first temporary storage unit 813 to the image acquisition unit 804 in accordance with the communication timing defined between the X-ray image transmission system 814 and the image acquisition unit 804. Upon receiving a retransmission request (first signal) for X-ray image data from the X-ray image reception system 815, the X-ray image transmission system 814 retransmits (re-output) the X-ray image data to the X-ray image reception system 815 in accordance with the retransmission request. When the image acquisition unit 804 completes the reception of the X-ray image data after the X-ray image data is output or re-output, the X-ray image transmission system 814 receives a signal (second signal) indicating the completion of the reception. The X-ray image reception system 815 repeats or continues image re-outputting operation in accordance with a retransmission request until the reception of the second signal.

However, it is undesirable to continue retransmission for a long period of time due to deterioration in communication quality, and so a retransmission time (specific time) is set as needed. In this case, the retransmission time is the time between the start of re-output and the interruption of the repetition of re-output. When the retransmission time elapses, the retransmission is interrupted even if the second signal has not been received.

The imaging apparatus control unit 806 sets such a retransmission time. When, in particular, the apparatus performs imaging operation while continuously switching a plurality of imaging modes such as the still image capturing mode and the moving image capturing mode (fluoroscopy or cine mode), the imaging apparatus control unit 806 sets a retransmission time based on the imaging mode after switching operation. This is processing for coping with the fact that priority is given to reliable transmission of an image sometimes and to transition to the next moving mode other times.

When performing positioning in moving image capturing operation or performing still image capturing with high image quality in consideration of a timing, the user gives priority to transition to a mode over reliable transmission of the last frame image (last image) of a moving image. In this case, the imaging apparatus control unit 806 sets a short retransmission time. Alternatively, the imaging apparatus control unit 806 sets the retransmission time to 0 to perform control so as not to perform re-output processing itself depending on the situation.

When, for example, the user switches to the moving image capturing mode after mask imaging in DSA imaging operation, since the priority of transition to the moving image capturing mode is low, the imaging apparatus control unit 806 sets a longer retransmission time for a still image in the first imaging mode than in the above case.

In addition, if, for example, the next imaging mode is not set at the end of moving image capturing, that is, the second imaging mode is not determined, the imaging apparatus control unit 806 sets a relatively long retransmission time as compared with a case in which the second imaging mode is determined.

The above processing by the imaging apparatus control unit 806 makes it possible to adaptively switch priority levels between reliable transfer of an image and switching to an imaging mode and support proper diagnosis and medical treatment using X-ray images. It is also possible to acquire images more suitable for a situation by setting a retransmission time based on both the first imaging mode and the second imaging mode.

In addition, the X-ray image transmission system 814 transmits an X-ray imaging start instruction to the X-ray generation control unit 808 at a proper timing (for example, the timing at which the operator inputs an X-ray imaging start instruction by using an operation unit (not shown)).

<Image Acquisition Unit 804>

The image acquisition unit 804 will be described next. The image acquisition unit 804 is a unit which stores the X-ray image acquired from the X-ray image transmission system 814 and sends it out to the display unit 805. The image acquisition unit 804 includes the X-ray image reception system 815, a second temporary storage unit 816, and a long-term storage unit 817.

The X-ray image reception system 815 is connected to the X-ray image transmission system 814 via a packet communication network such as Ethernet®. The X-ray image reception system 815 acquires an X-ray image from the imaging apparatus control unit 806 by communicating with the X-ray image transmission system 814 via this network, and stores the acquired X-ray image in the second temporary storage unit 816. It is possible to provide a technique like that disclosed in Japanese Patent Laid-Open No. 2010-088027 for this communication. As shown in FIG. 8, the X-ray image reception system includes, in addition to the a reception unit 851 and the retransmission requesting unit 852, a packet loss determination unit 853, a reception completion determination unit 854, a database 855 and a retransmission setting determination unit 856.

Note that the X-ray image reception system 815 transmits a transmission request (first signal) to the X-ray image transmission system 814 upon detecting the occurrence of an error at the time of this communication. Upon receiving this retransmission request, the X-ray image transmission system 814 retransmits an X-ray image. The X-ray image reception system 815 receives this retransmitted X-ray image and stores it in the second temporary storage unit 816. The X-ray image temporarily stored in the second temporary storage unit 816 is stored and saved in the long-term storage unit 817. The X-ray image reception system 815 can also transmit the acquired X-ray image to the display unit 805.

<Display Unit 805>

The display unit 805 serves to display various kinds of image information including the X-ray images transmitted from the X-ray image reception system 815 and character information, and is formed from a CRT, liquid crystal display, or the like. FIG. 8 shows the display unit 805 integrated with the X-ray imaging apparatus 818. However, the display unit 805 is not limited to this arrangement, and may be a device independent of the X-ray imaging apparatus 818.

<Operation Timing of X-Ray Imaging Apparatus 818>

The operation timing of the X-ray imaging apparatus 818 will be described next. The X-ray imaging apparatus 818 can set either a still image mode as an imaging mode for capturing one (one frame) X-ray image or a moving image mode as an imaging mode for capturing a plurality (a plurality of frames) of X-ray images by continuously capturing X-ray images. Image mode setting is implemented by making the imaging apparatus control unit 806 set the imaging mode input by the operator operating an operation unit (not shown).

Figure 2:
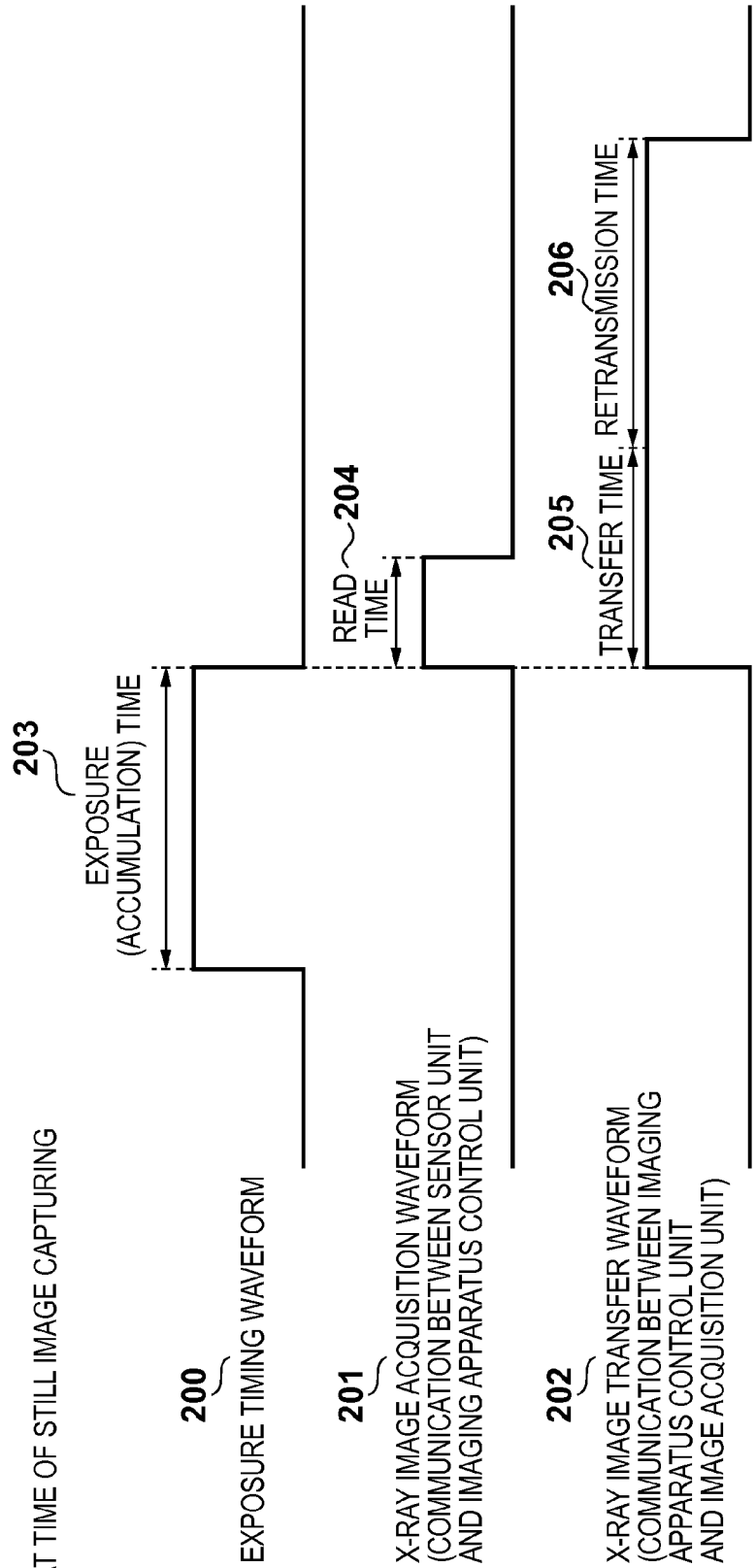
FIG. 2 is a view for explaining the operation of an X-ray imaging apparatus 818 when the still image mode is set.

The operation of the X-ray imaging apparatus 818 in a case in which the still image mode is set will be described first with reference to FIG. 2. FIG. 2 shows the operation of each constituent element to be described in the following description as a waveform.

A waveform 200 represents an X-ray emission period of the X-ray generator 807, and an exposure time 203 (high period) represents an X-ray emission period. Note that this period is also the period during which the flat panel detector 809 detects X-rays.

A waveform 201 represents a period during which the imaging apparatus control unit 806 acquires an X-ray image from the sensor unit 803, and a read time 204 (high period) corresponds to this period. The read time 204 starts when an X-ray emission period of the X-ray generator 807 comes to an end (the end of an X-ray detection period of the flat panel detector 809) and the X-ray image generating unit 811 completes the generation of an X-ray image.

A waveform 202 represents a period (high period) during which the X-ray image transmission system 814 transfers (retransmits) an X-ray image to the X-ray image reception system 815. Referring to FIG. 2, in this period, since the X-ray image transmission system 814 has transferred one X-ray image within the first period (transfer time 205) but an error has occurred in this transfer, the X-ray image transmission system 814 retransmits the one X-ray image in the next period (retransmission time 206).

The transfer time 205 starts together with the start of the read time 204. That is, when an X-ray emission period of the X-ray generator 807 comes to an end and the X-ray image generating unit 811 completes the generation of an X-ray image, the imaging apparatus control unit 806 starts acquiring an X-ray image from the sensor unit 803 and simultaneously starts transferring the X-ray image.

If this transfer succeeds (as long as no retransmission request is received from the X-ray image reception system 815), there is no need for the X-ray image transmission system 814 to perform any specific operation during the retransmission time 206. If a transfer error has occurred and the X-ray image reception system 815 transmits a retransmission request to the X-ray image transmission system 814 upon detecting the error, the X-ray image transmission system 814 retransmits an X-ray image to the X-ray image reception system 815 during the retransmission time 206 (within the retransmission time). This retransmission comes to an end when the error is eliminated or the retransfer times out as the retransmission time 206 assigned to the retransmission elapses.

Note that the retransmission time 206 may be obtained in advance as the time obtained by subtracting the exposure time 203 and the transfer time 205 from the period assigned to one X-ray image in advance or may be set to a proper time. In any case, the retransmission time 206 is obtained in advance by using some kind of method as the retransmission time used when the still image mode is set, and is held in the imaging apparatus control unit 806 in advance.

Obviously, the image acquisition unit 804 may set and hold retransmission time information. For example, the storage unit of the image acquisition unit 804 holds lookup table information or function information for obtaining a retransmission time corresponding to the second imaging mode after switching operation when the apparatus operates in the first imaging mode before the switching operation. The image acquisition unit 804 sets a retransmission time based on the held information and transmits a signal (first signal) to the imaging apparatus control unit 806 together with a retransmission request.

Figure 3:
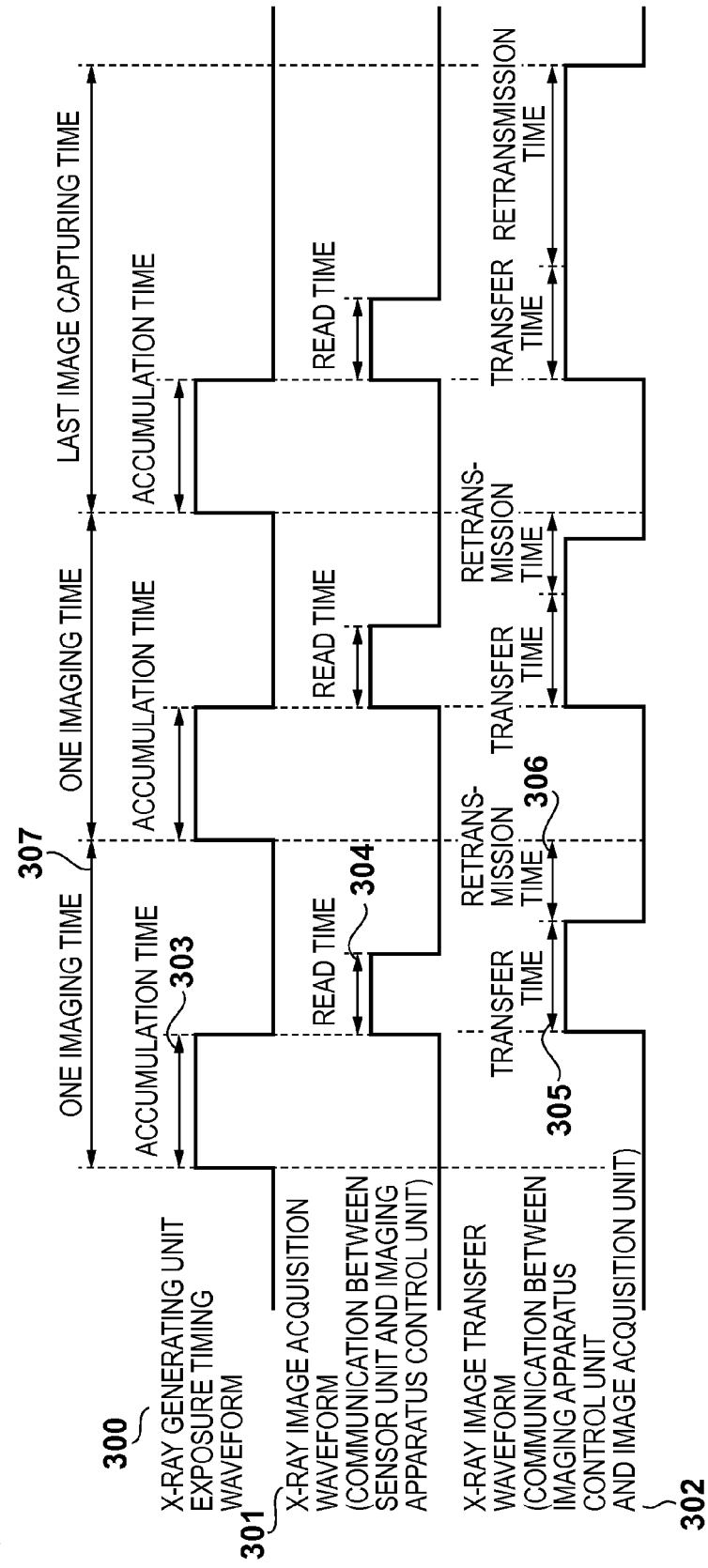
FIG. 3 is a view for explaining the operation of the X-ray imaging apparatus 818 when the moving image mode is set.
Figure 4:
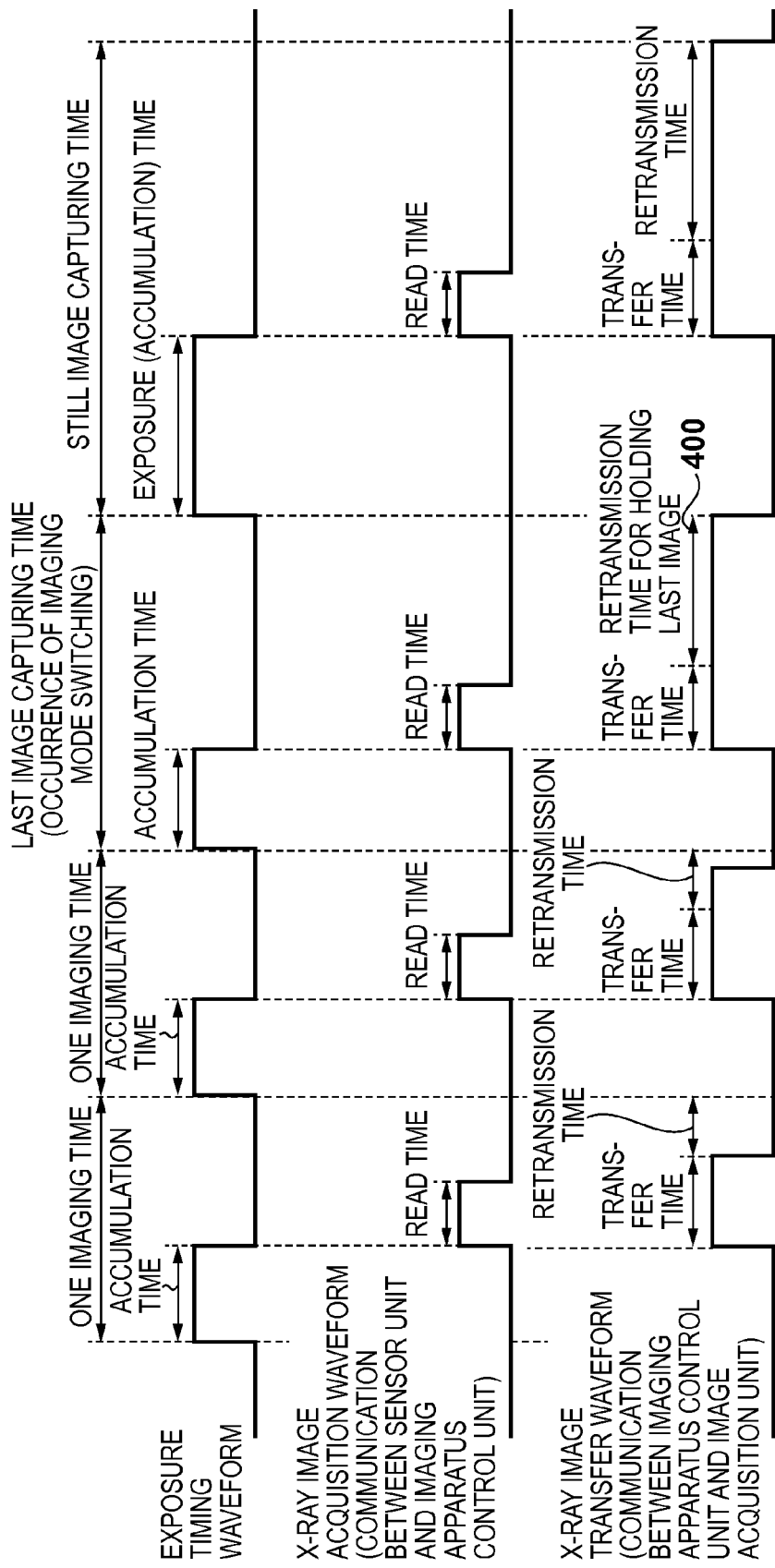
FIG. 4 is a view for explaining signal waveforms.

The operation of the X-ray imaging apparatus 818 in a case in which the moving image mode is set will be described next with reference to FIG. 3. FIG. 3 shows the operation of each constituent element to be described in the following description as a waveform.

A waveform 300 represents an X-ray emission period of the X-ray generator 807, and accumulation time 303 (high period) represents an X-ray emission period. Note that this period is also the period during which the flat panel detector 809 detects X-rays. In the moving image mode, since the apparatus continuously captures a plurality of X-ray images, the accumulation time 303 repeatedly appears.

A waveform 301 represents a period during which the imaging apparatus control unit 806 acquires an X-ray image from the sensor unit 803, and a read time 304 (high period) corresponds to this period. The read time 304 starts when an X-ray emission period of the X-ray generator 807 comes to an end (the end of an X-ray detection period of the flat panel detector 809) and the X-ray image generating unit 811 completes the generation of an X-ray image.

A waveform 302 represents a period (high period) during which the X-ray image transmission system 814 transfers (retransmits) an X-ray image to the X-ray image reception system 815. In this case, one imaging time 307 is the imaging timing interval between adjacent frames which is determined by an imaging rate. For this reason, the period from the end of a transfer time 305 (after the transfer) to the end timing of the one imaging time 307 is assigned to a period (retransmission time 306) during which retransmission can be performed when a transfer error occurs.

That is, the retransmission time 306 is the time obtained by subtracting the accumulation time 303 and the transfer time 305 from the one imaging time 307, which can be obtained in advance. Assume that the retransmission time 306 is obtained in advance as a retransmission time used when the moving image mode is set, and is held in the imaging apparatus control unit 806. Note that it is possible to assign, for example, 80% of this time to the retransmission time 306 without assigning the entire time to the retransmission time 306. If the transfer time is variable, a retransmission time needs to be calculated for each transmission operation.

Referring to FIG. 3, since the transfer of the first X-ray image has succeeded (no retransmission request has been received from the X-ray image reception system 815), no retransmission is performed in the retransmission time 306. However, since the transfer of the second and third X-ray images has failed, the apparatus retransmits X-ray images in the retransmission time 306 after the transfer time 305.

In this manner, when an X-ray emission period of the X-ray generator 807 comes to an end and the X-ray image generating unit 811 completes the generation of an X-ray image, the imaging apparatus control unit 806 starts acquiring the X-ray image from the sensor unit 803 and starts transferring the X-ray image. If this transfer succeeds, there is no need for the X-ray image transmission system 814 to perform any specific operation during the retransmission time 306. If a transfer error has occurred and the X-ray image reception system 815 transmits a retransmission request to the X-ray image transmission system 814 upon detecting the error, the X-ray image transmission system 814 retransmits an X-ray image to the X-ray image reception system 815 during the retransmission time 306.

Note that retransmission comes to an end when the error is eliminated or the retransfer times out as the retransmission time 306 assigned to the retransmission elapses. The imaging operation timing is basically the same as that in the still image capturing mode. However, the one imaging time 307 is determined by the frame rate of imaging in the moving image capturing mode, which in turn determines the maximum value of the retransmission time 306.

Figure 5:
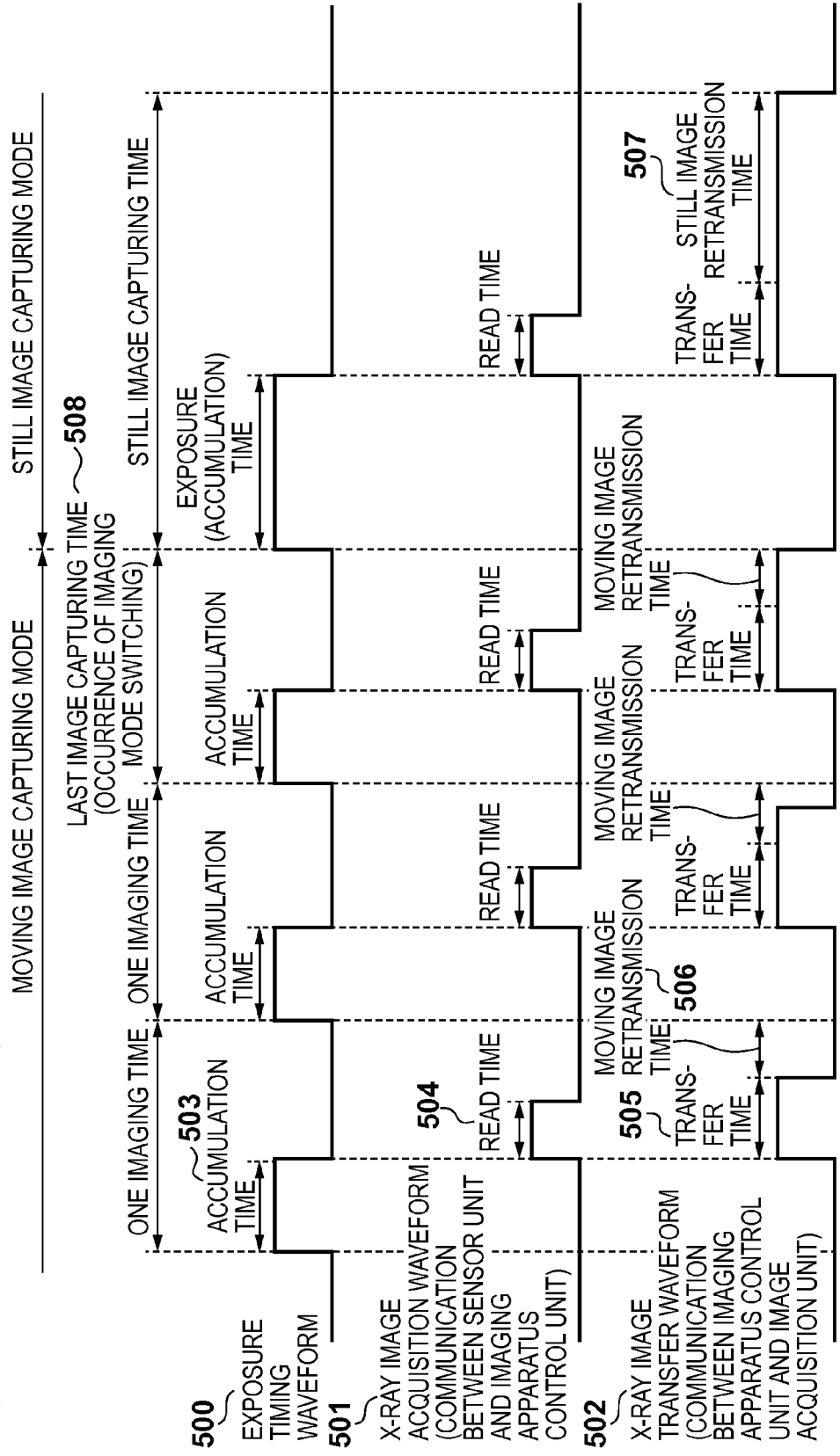
FIG. 5 is a view for explaining the operation of the X-ray imaging apparatus 818.

The X-ray imaging apparatus 818 can perform X-ray imaging in accordance with each imaging mode in this manner. The operation of the X-ray imaging apparatus 818 which performs X-ray imaging while switching these imaging modes at an arbitrary timing will be described next with reference to FIG. 5. FIG. 5 shows the operation of each constituent element to be described in the following description as a waveform. Note that the X-ray image transmission system 814 can set a retransfer timeout time in accordance with each imaging mode.

Referring to FIG. 5, the moving image mode is set first, and the still image mode is set during capturing of the third X-ray image to make the apparatus capture the fourth image in the still image mode. At this time, obviously, it is necessary to change the retransmission time to be used from the retransmission time for the moving image mode to the retransmission time for the still image mode. The timing of this change is set at the end of an imaging period (an imaging period for the third X-ray image in the case of FIG. 5) in which the still image mode is changed or the time when the imaging mode is switched at a time other than the imaging time. Obviously, the timing of this change is not limited to this.

A waveform 500 represents an X-ray emission period of the X-ray generator 807, and an accumulation time 503 (high period) represents an X-ray emission period. Note that this period is also the period during which the flat panel detector 809 detects X-rays.

A waveform 501 represents a period during which the imaging apparatus control unit 806 acquires an X-ray image from the sensor unit 803, and a read time 504 (high period) corresponds to this period. The read time 504 starts when an X-ray emission period of the X-ray generator 807 comes to an end (the end of an X-ray detection period of the flat panel detector 809) and the X-ray image generating unit 811 completes the generation of an X-ray image.

A waveform 502 represents a period (high period) during which the X-ray image transmission system 814 transfers (retransmits) an X-ray image to the X-ray image reception system 815. Referring to FIG. 5, since the transfer of the first X-ray image has succeeded, the apparatus performs no retransmission in a retransmission time 506. However, since the transfer of the second and third X-ray images has failed, the apparatus retransmits X-ray images in the retransmission time 506 after the end of a transfer time 505.

In this case, since the still image mode is set in the imaging period of the third X-ray image (a last image capturing time 508), the X-ray image transmission system 814 changes the currently used retransmission time from the retransmission time 506 for the moving image mode to a retransmission time 507 for the still image mode.

In this embodiment, the retransfer timeout time is changed at the time of switching between the imaging modes. However, other parameters may be changed at the same timing. In the moving image mode, a retransfer timeout instruction is issued every time one imaging time elapses.

The retransmission time in an imaging mode of acquiring an image displayed on the screen for only a short period of time without being stored as in fluoroscopy is set to be short in advance. This shortens the time of switching to the next imaging mode even if retransfer occurs when the last image is output at the time of switching between the imaging modes. This will reduce the difference between an image to be stored and an image which is checked when the operator performs still image capturing at an arbitrary timing and stores the captured image while checking the movement of the object on a fluoroscopic image.

Note that in this embodiment, the transfer destination of an X-ray image obtained by the X-ray image transmission system 814 is the X-ray image reception system 815. However, the transfer destination is not limited to this, and may be any functional unit which handles transferred X-ray images and can detect an error in the transfer and notify the X-ray image transmission system 814 of the error.

Second Embodiment

Figure 1:
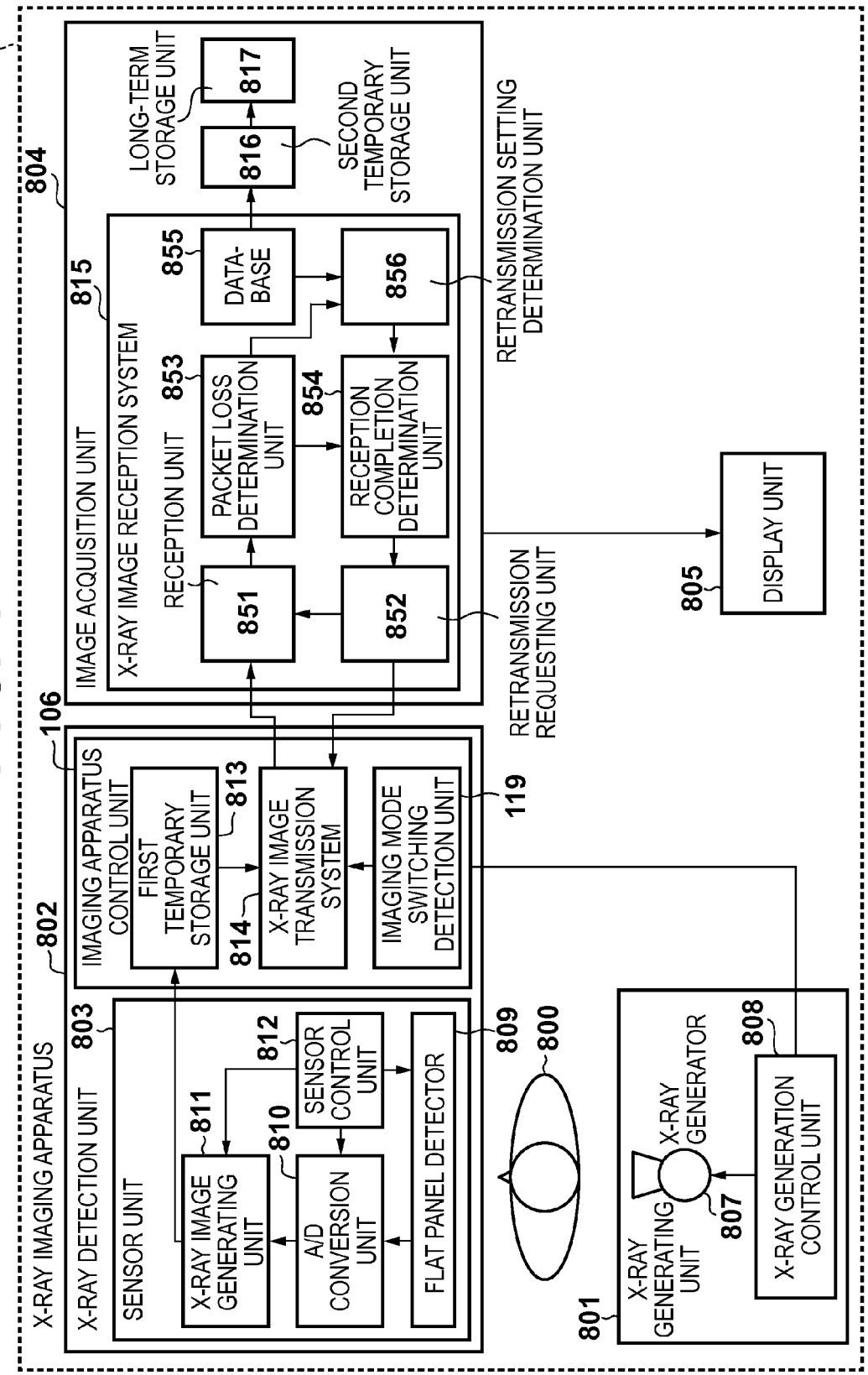
FIG. 1 is a block diagram showing an example of the arrangement of an X-ray imaging apparatus.

FIG. 1 shows an example of the arrangement of an X-ray imaging apparatus according to the second embodiment. The arrangement shown in FIG. 1 is the same as that in the first embodiment except that an imaging apparatus control unit 106 is used as an arrangement obtained by adding an imaging mode switching detection unit 119 to an imaging apparatus control unit 806 in the arrangement in FIG. 8. The imaging mode switching detection unit 119 determines whether the imaging modes have been switched, and notifies an X-ray image transmission system 814 of the determination result. Note that only portions different from the first embodiment will be described, and any points to which no particular reference is made are the same as in the first embodiment.

Figure 6:
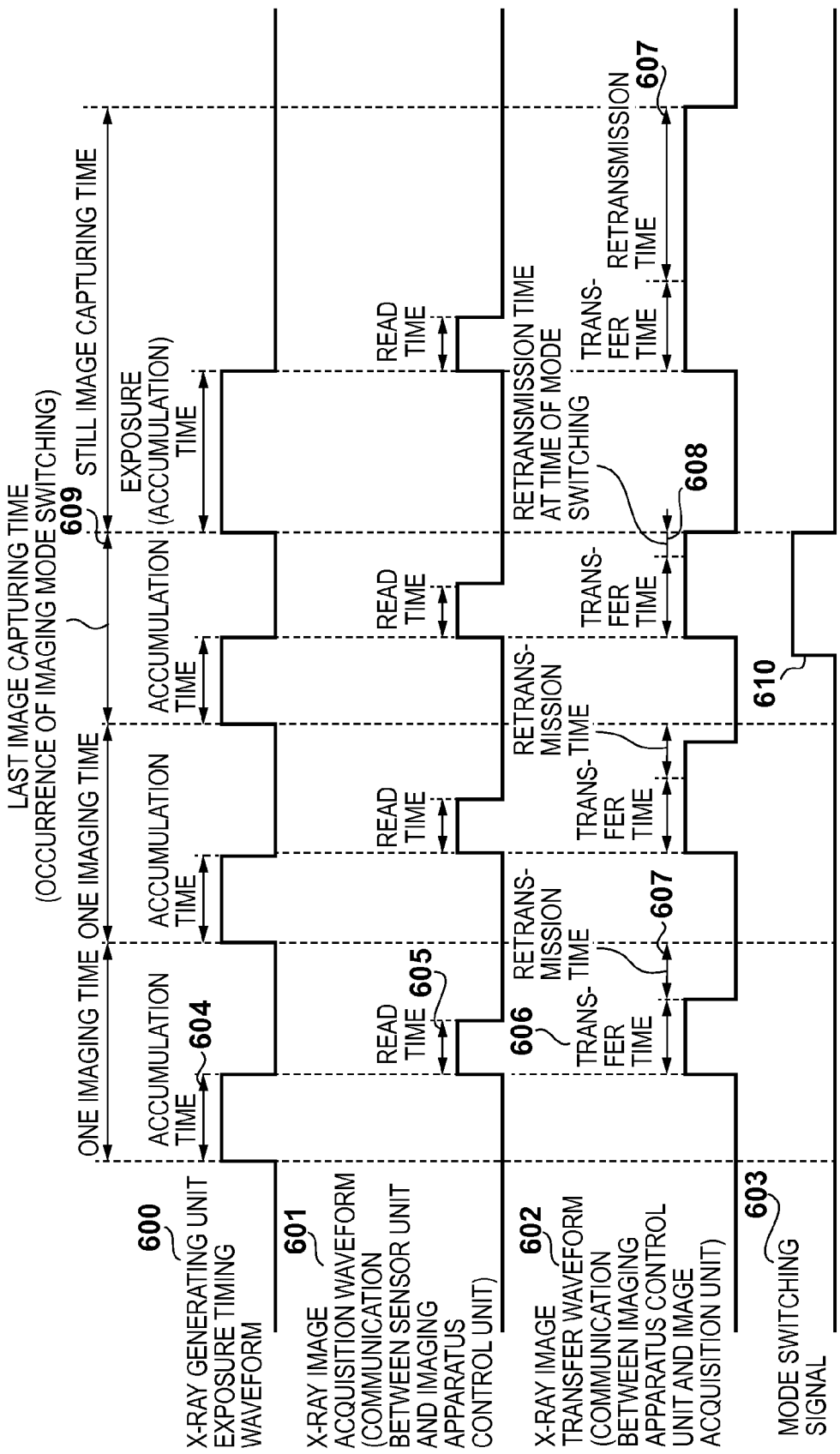
FIG. 6 is a view for explaining the operation of the X-ray imaging apparatus 818.

The operation of an X-ray imaging apparatus 118 which performs X-ray imaging while switching the imaging modes in the same manner as that shown in FIG. 5 will be described next with reference to FIG. 6. Referring to FIG. 6, like FIG. 5, the moving image mode is set first, and the still image mode is set during capturing of the third X-ray image to make the apparatus capture the fourth image in the still image mode.

Waveforms 600 and 601 in FIG. 6 are identical to the waveforms 500 and 501 in FIG. 5, and respectively include accumulation time 604 and read time 605, as shown.

A waveform 603, which as shown includes a transfer time 606, represents a period (high period) during which the imaging mode switching detection unit 119 detects switching between the imaging modes. This period corresponds to a period 610. The period 610 is the period from the detection of switching between the imaging modes to the end of a last image capturing time 609.

A waveform 602 is identical to the waveform 502 except for a portion at the time of capturing of three X-ray images. Since the waveform 603 is at high level (period 610) at the time of capturing of the third X-ray image, the retransmission time is set to a time 608 shorter than a retransmission time 607 for the moving image mode. More specifically, as a retransmission time immediately after the detection of switching from one of the moving image mode and the still image mode to the other imaging mode, a retransmission time shorter than the retransmission time set in the moving image mode and the retransmission time set in the still image mode is set. In a still image capturing time, a retransmission time is set to the retransmission time 607 for the still image mode. Assume that the imaging apparatus control unit 106 also holds the time 608.

This embodiment quickens imaging mode switching by setting the time 608 shorter than the normal retransmission time 607 (the retransmission time for the moving image mode or the retransmission time for the still image mode) or the time by which a retransfer timeout instruction in the moving image mode is issued. Since it is possible to perform retransfer up to the maximum time in each mode in the absence of imaging mode switching, it is possible to reduce a deterioration in image quality due to an image transfer error in each mode. In addition, since the normal retransmission time is set at the end of imaging operation without no imaging mode switching, it is possible to reduce an image transfer error in the last image even in the moving image capturing operation as compared with the first embodiment.

Third Embodiment

In addition to the arrangement of the second embodiment, the third embodiment is configured to determine, upon detecting imaging mode switching via a imaging mode switching detection unit 119, whether the imaging mode after the switching operation is the still image mode or the moving image mode.

Upon determining that the imaging mode after the switching operation is the imaging mode of quickly performing imaging, the embodiment sets a retransmission time 608. On the other hand, upon determining that the imaging mode after the switching operation is the imaging mode which is not required to quickly perform imaging, the embodiment sets a normal retransmission time 607.

This arrangement can ensure the sufficient retransmission time 607 except when the imaging mode is switched to the imaging mode of quickly performing imaging. This makes it possible to reduce a deterioration in image quality due to a transfer error as compared with the second embodiment.

Fourth Embodiment

The fourth embodiment is a modification of the second embodiment, and differs from the second embodiment in only the operation of an X-ray imaging apparatus to be described below. Any points to which no particular reference is made are the same as in the second embodiment.

Figure 7:
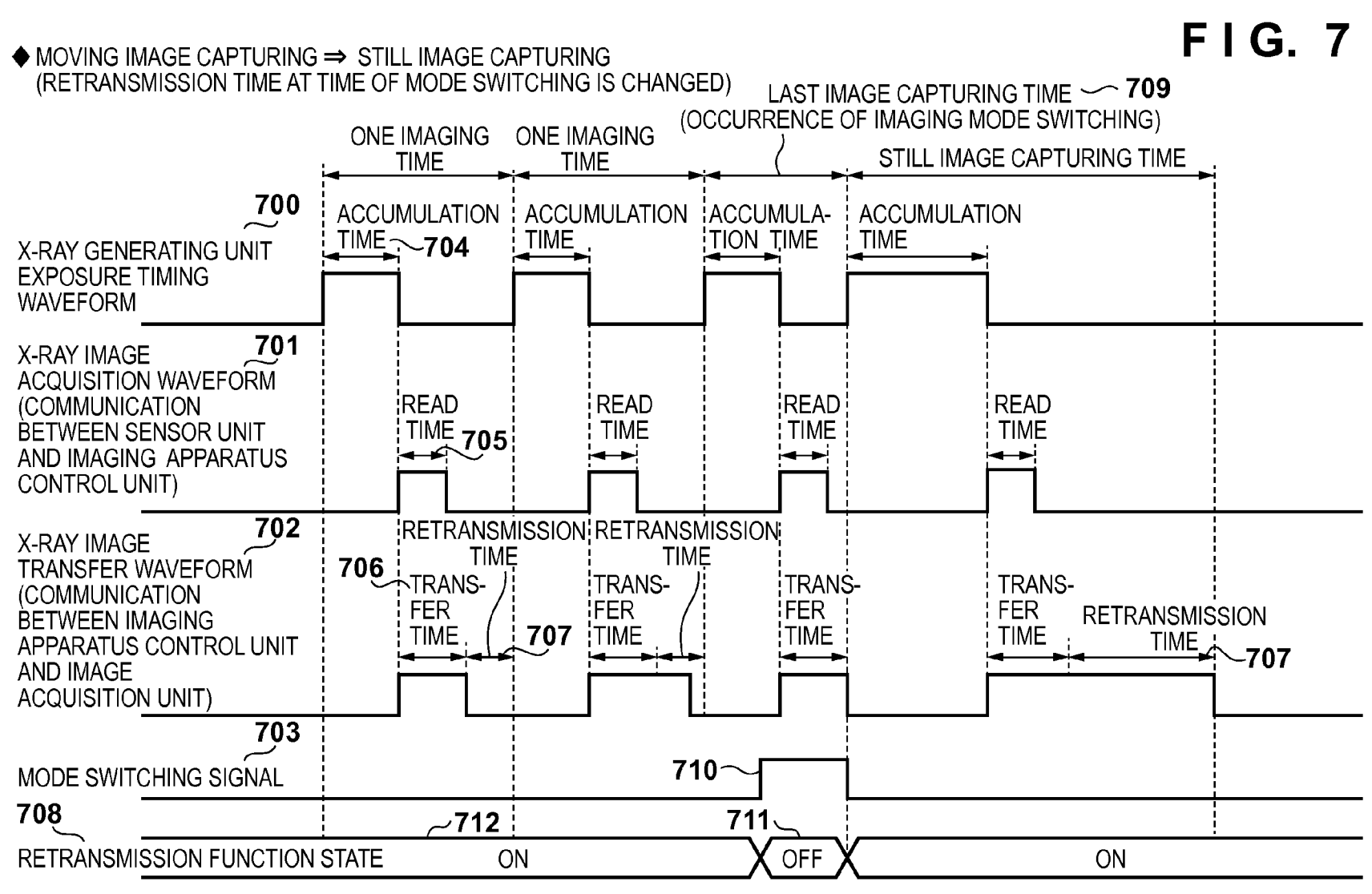

The operation of an X-ray imaging apparatus 118 which performs X-ray imaging operation while switching the imaging modes in the same manner as shown in FIG. 5 will be described next with reference to FIG. 7. Referring to FIG. 7, like FIG. 5, the moving image mode is set first, and the still image mode is set during capturing of the third X-ray image to make the apparatus capture the fourth image in the still image mode.

Waveforms 700, 701, and 703 are identical to the waveforms 600, 601, and 603 in FIG. 6, and respectively include accumulation time 704, read time 705 and transfer time 706, and in addition, last image capturing time 709 and retransmission time 707, as shown. A waveform 708 is a signal waveform for switching on or off a retransmission time setting function. Referring to FIG. 7, since this function is switched on in an imaging period 712 for the first and second X-ray images, a retransmission time is set as indicated by a waveform 702. In contrast, since the function is switched off in an imaging period 711 for the third X-ray image, no retransmission time is set as indicated by the waveform 702. That is, 0 is set in this period. Assume that an X-ray image transmission system 814 switches on and off the retransmission time setting function.

As described above, at the time of imaging mode switching, it is possible to switch to the next imaging mode without being influenced by retransfer when the transfer time for an image ends. This shortens the mode switching time as compared with the first and second embodiments, and hence can ensure a sufficient retransfer time in the absence of image mode switching, thereby reducing a deterioration in image quality due to an image transfer error in each mode.

Fifth Embodiment

The fifth embodiment performs LIH retransfer control in accordance with adjustment to keep the switching time for imaging mode switching constant. When mode switching occurs immediately after X-ray emission, it is necessary to provide for diagnosis the image obtained by exposure with emitted X-rays, in order to prevent the exposure from becoming invalid exposure which generates no image. For this purpose, the apparatus performs imaging mode switching after reading the image signal obtained based on the X-rays from a flat panel detector 809 and outputting the obtained image to an image acquisition unit 804. In contrast, if mode switching occurs at the timing when the transfer of an image is almost complete, the apparatus starts performing imaging mode switching after the end of the image transfer. Assume that the apparatus performs imaging upon switching between a plurality of imaging modes in this manner. In this case, if an instruction to set the second imaging mode is issued during operation in the first imaging mode, the time required for mode transition processing varies depending on the state of the system.

In this manner, therefore, a standby time is inserted in accordance with the state of the imaging system upon reception of an instruction so as to adjust the imaging mode switching time. When executing such adjustment control, the apparatus can ensure a retransfer time while reducing variations in imaging mode switching time by setting the retransfer time for an LIH image to a time that does not exceed the standby time.

Figure 9:
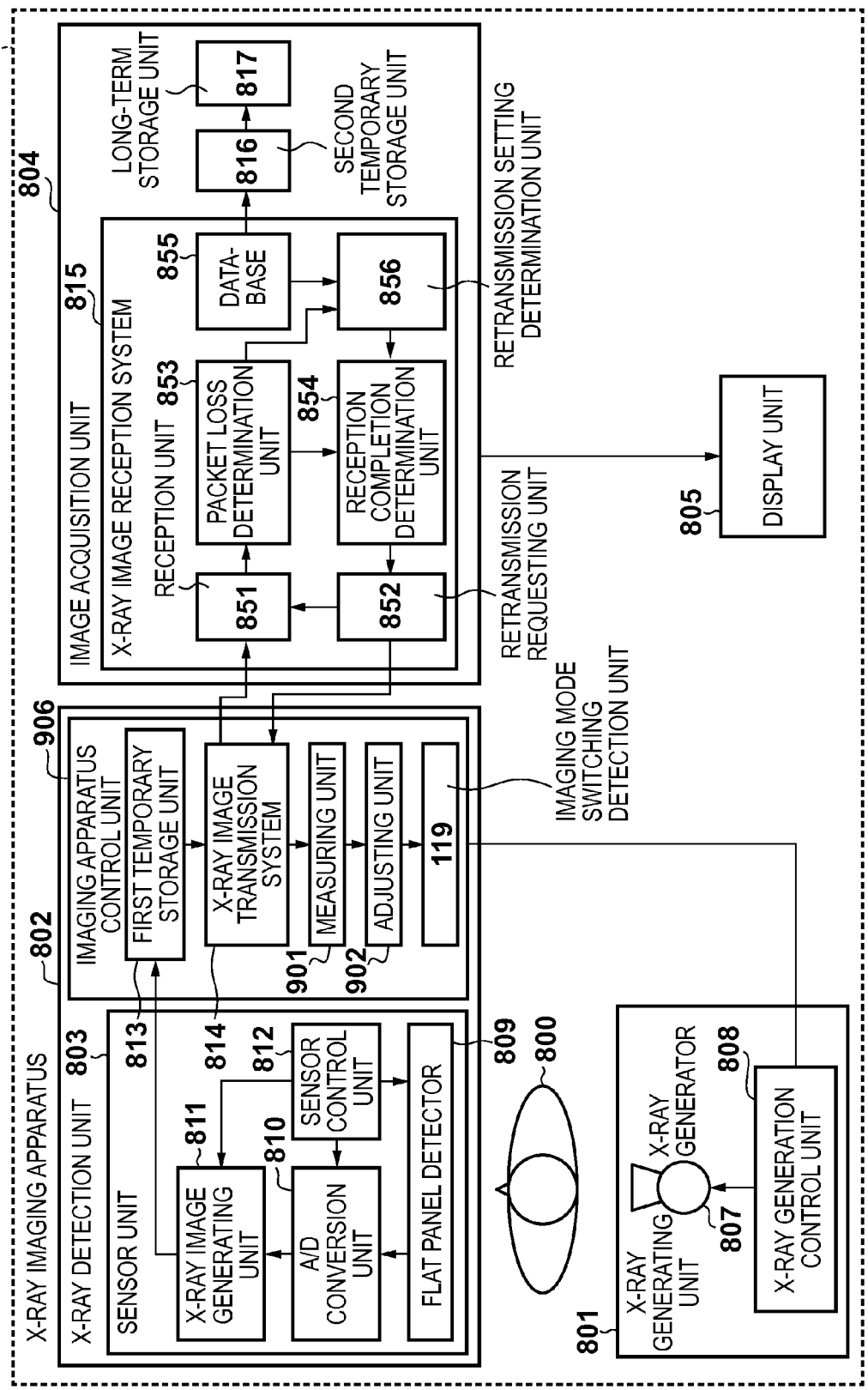
FIG. 9 is a block diagram showing an example of the arrangement of an X-ray imaging apparatus according to the fifth embodiment.

As shown in FIG. 9, the arrangement of this embodiment differs from that of the second embodiment in that an imaging apparatus control unit 906 includes a measuring unit 901 and an adjusting unit 902. In addition, the imaging apparatus control unit 906 executes control to make transition to the second imaging mode stand by for at least a determined standby time and control to execute mode transition processing from the first imaging mode to the second imaging mode.

Upon detection of the occurrence of imaging mode switching, the measuring unit 901 measures a time Tf until the end of imaging in the mode before mode switching. The adjusting unit 902 adjusts the time until switching to the next imaging mode. More specifically, the adjusting unit 902 determines a standby time Tw corresponding to the time Tf. That is, the adjusting unit 902 determines a standby time corresponding to the state of the imaging system at the time of reception of the above instruction, and determines a standby time in accordance with the measured time. This standby time serves to compensate for variations in the measured time Tf so as to keep constant the time from the instant an imaging mode switching instruction is issued to the instant the current imaging mode is switched and imaging in the next imaging mode is started. Obviously, it is not always required to keep the above time constant because of the influence of mode transition on the generating apparatus side, and the standby time Tw is set to reduce variations in the time required for mode transition.

If the mode transition time on the X-ray generating unit side varies, it is possible to make the standby time Tw take on significance in terms of reducing the variations. Variations in mode transition time for the X-ray generating unit are grasped in advance with proper accuracy and stored in a memory, and the standby time Tw is set to make the flat panel detector 809 stand by in consideration of the maximum value, average value, or the like of mode transition times. For example, the standby time Tw is set to complete mode transition for the flat panel detector 809 within a time equal to the average value of the mode transition times for the X-ray generating unit. That is, the imaging apparatus control unit 906 determines a standby time so as to make the time required for the completion of transition to an imaging mode upon reception of an instruction approach a fixed value regardless of the timing of issuance of an instruction in accordance with the driving state of the imaging system at the time of reception of the instruction. A standby time may be determined by using a calculation formula defined in advance or based on a lookup table for determining Tw corresponding to the value of Tf. The imaging apparatus control unit 906 determines different times as standby times depending on situations. Examples of the situations in this case include a case in which an instruction is used during an accumulation period for electrical signals corresponding to the detection of light or radiation by the sensor of the imaging system and a case in which an instruction is issued during the transfer of data based on read electrical signals.

The set standby time Tw is output (transmitted) to a reception unit 851 of an X-ray image reception system 815 via the transmission unit of an X-ray image transmission system 814. The reception unit 851 receives the information of the standby time Tw, and a retransmission setting determination unit 856 sets a retransmission time based on the standby time Tw by using lookup table information and the like stored in the storage unit. A retransmission requesting unit (transmission unit) 852 transmits the set standby time Tw to the imaging apparatus control unit 906.

The X-ray image transmission system 814 of the imaging apparatus control unit 906 receives such retransmission time information. The imaging apparatus control unit 906 controls the retransfer of an image. Providing retransmission time setting processing on the X-ray detection unit 802 side instead of the image acquisition unit 804 can shorten the time required for inquiry and reception of a retransmission time.

Figure 10:
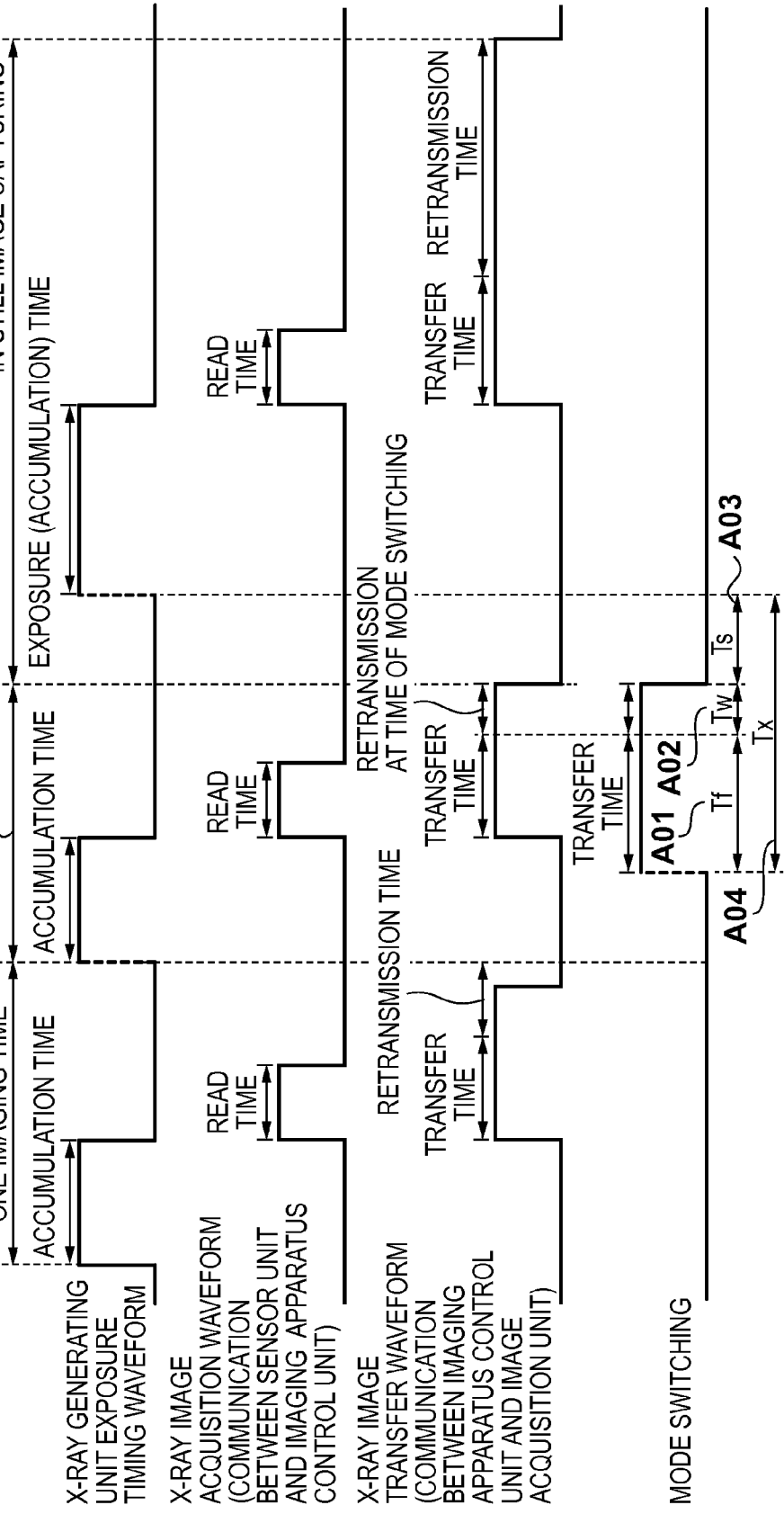
FIG. 10 is a view for explaining the operation of the X-ray imaging apparatus according to the fifth embodiment.

FIG. 10 shows an example of operation timings in this embodiment. The X-ray detection unit in this embodiment is configured to suppress variations in the time from the detection of imaging mode switching to the execution of imaging in the next imaging mode. This mechanism will be described below.

Let Tx be a time A04 from the detection of imaging mode switching to the execution of imaging, Ts be a preparation time A03 for imaging in the imaging mode after switching, Tf be a time A01 from the detection of imaging mode switching to the end of the first imaging mode, and Tw be a time A02 from the end of the first imaging mode to the start of the second imaging mode. The relationship between the above times is expressed by $$Tx = Tf + Tw + Ts$$

Adjusting Tw can keep constant the shortest time Tx from the detection of imaging mode switching to the execution of imaging in the next imaging mode. The following conditions are required to keep the shortest time Tx after imaging mode switching constant by adjusting Tw. However, let Fr be the time taken for one imaging operation in the first imaging mode.

$$Tx \leq Tf + Ts$$

$$Tf \leq Fr$$

This embodiment generates a retransfer timeout at the start of the second imaging mode. In the embodiment, setting the shortest imaging time Tx after imaging mode switching based on conditions can reduce variations in time due to imaging mode switching. In addition, it is possible to prevent a delay in imaging in the second imaging mode due to retransfer and to perform optimal retransfer in accordance with the timing of the occurrence of imaging mode switching. This embodiment is effective when it is necessary to perform imaging preparation processing before the start of imaging after imaging mode switching.

Note that the first to fifth embodiments may be combined as needed. When combining the embodiments, several functions may be omitted or changes and modifications may be made.

Sixth Embodiment

According to the embodiment described above, the X-ray imaging apparatus incorporates the X-ray detection unit 802 and the image acquisition unit 804. In addition to this, the embodiment incorporates a radiation imaging system including, as discrete devices, a device having the function of the image acquisition unit 804 and a radiation detection device having the function of the X-ray detection unit 802.

In this case, the radiation detection apparatus includes a radiation detector having the function of the flat panel detector 809, an output unit having part of the function of the X-ray image transmission system, and a control unit having part of the function of the imaging apparatus control unit 806. The output unit outputs radiation image data based on the image signal obtained by the radiation detector to an external device. The external device in this case is a radiation image acquisition device having the function of the image acquisition unit 804. However, this device may be a device for displaying other kinds of images.

The control unit performs control to make the output unit start re-outputting radiation image data in accordance with the first signal from an external device. The external device in this case may be a control device having the function of the image acquisition unit 804, or may be a control device which transmits the first signal for requesting re-outputting operation.

The control unit determines whether information designating specific image information is added to the first signal. Upon determining that such information is added, the control unit transmits only the data of a portion, of radiation image data, which corresponds to the specific image information. This can reduce re-outputting operation for unnecessary data. The control unit then receives the second signal from the external device or continues the above re-outputting operation until the elapse of a specific time from the start of the re-outputting operation. In addition, it is possible to apply the control operations and functions in the first to fifth embodiments described above to the radiation imaging system according to the sixth embodiment.

OTHER EMBODIMENTS

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-047302 filed Mar. 2, 2012 which is hereby incorporated by reference herein in its entirety.

What is claimed is:

1. A control device which performs radiation imaging by controlling a digital radiation imaging apparatus, the device comprising:
a detection unit which detects an imaging instruction in a specific imaging mode;
a transferring unit which performs a transfer of outside radiation image data obtained by the digital radiation imaging;
a control unit which executes retransmission processing within a retransmission timeout time when the transfer fails; and
a setting unit which sets, in a first imaging mode, a retransmission timeout time limit for an item of image data that is to be transferred last, in a time sequence of image data transfer, to be different from a retransmission timeout time limit for at least one other item of image data to be transferred.

2. The device according to claim 1, wherein said setting unit sets, as a retransmission timeout time limit for the image data transferred last, a value larger than a retransmission timeout time for the at least one other item of image data.

3. The device according to claim 1, wherein said setting unit sets, as a retransmission timeout time limit for the image data transferred last, a value smaller than a retransmission timeout time limit for the at least one other item of image data or 0.

4. A method of controlling a control device which performs radiation imaging by controlling a digital radiation imaging apparatus, the method comprising:
a detection step of detecting an imaging instruction in a specific imaging mode;
a transferring step of performing a transfer of outside radiation image data obtained by the digital radiation imaging;
a control step of executing retransmission processing within a retransmission timeout time when the transfer fails; and
a setting step of setting, in a first imaging mode, a retransmission timeout time limit for an item of image data that is to be transferred last, in a time sequence of image data transfer, to be different from a retransmission timeout time limit for at least one other item of image data to be transferred.

5. An X-ray imaging apparatus comprising:
an X-ray image generating unit which detects X-rays transmitted through an object and generates an X-ray image of the object based on the detected X-rays; and
a control unit which acquires the X-ray image from said X-ray image generating unit and transfers the X-ray image to a functional unit which processes the X-ray image,
wherein said control unit retransmits, to the functional unit, one X-ray image acquired by said X-ray image generating unit within a preset retransmission time, when a retransmission request for the X-ray image is received from the functional unit after the X-ray image is transferred to the functional unit,
wherein said control unit sets, as the retransmission time, a period until a start of capturing of a next X-ray image after the transfer, when a moving image mode for capturing a plurality of X-ray images by continuously capturing X-ray images is set, and
wherein said control unit sets a predetermined time as the retransmission time when a still image mode for capturing one X-ray image is set.

6. The apparatus according to claim 5, wherein the functional unit transmits the retransmission request to said control unit when an error in the transfer is detected.

7. The apparatus according to claim 5, wherein said control unit sets a retransmission time shorter than a retransmission time set in a moving image mode and a retransmission time set in a still image mode as a retransmission time immediately after detection of switching from one of the moving image mode and the still image mode to the other.

8. A radiation imaging apparatus comprising:
a radiation detector which obtains an image signal by detecting radiation;
an output unit which outputs radiation image data based on the image signal to an external device;
a control unit which makes said output unit start re-outputting at least part of the radiation image data in accordance with a first signal from an external device, and receives a second signal from the external device or continues the re-outputting until elapse of a specific time from a start of the re-outputting; and
a setting unit which sets the specific time based on selection of a second imaging mode executed sequentially after a first imaging mode of radiation imaging for obtaining the image signal.

9. The apparatus according to claim 8, wherein said setting unit sets, based on the second imaging mode, the specific time concerning radiation image data to be captured or transferred last concerning radiation image data obtained in the first imaging mode.

10. The apparatus according to claim 8, wherein said setting unit sets the specific time based on the first imaging mode and the second imaging mode.

11. The apparatus according to claim 10, wherein said setting unit sets the specific time to a shorter time than when the second imaging mode is not set, if the first imaging mode is moving image capturing and the second imaging mode is still image capturing.

12. The apparatus according to claim 11, wherein said setting unit makes setting to eliminate the specific time if the first imaging mode is moving image capturing and the second imaging mode is still image capturing.

13. The apparatus according to claim 8, further comprising a detection unit which detects an imaging mode switching instruction,
wherein said control unit provides a standby time when switching the imaging mode, and
said setting unit sets the specific time to a time which does not exceed the standby time when said detection unit detects an instruction to switch from the first imaging mode to the second imaging mode.

14. A control device comprising:
a reception unit which receives image data from a radiation detector;
a transmission unit which transmits, to said radiation detector, a signal for requesting retransmission of the image data and a signal indicating a retransmission time for interrupting retransmission of the image data before completion of the retransmission; and
a setting unit which sets the retransmission time based on selection of a first imaging mode of radiation imaging for obtaining the image data and a second imaging mode executed sequentially after the first imaging mode.

15. A method of controlling an X-ray imaging apparatus including an X-ray image generating unit which detects X-rays transmitted through an object and generates an X-ray image of the object based on the detected X-rays, and a control unit which acquires the X-ray image from the X-ray image generating unit and transfers the X-ray image to a functional unit which processes the X-ray image, the method comprising:
a retransmitting step, in which the control unit retransmits, to the functional unit, one X-ray image acquired by the X-ray image generating unit within a preset retransmission time, when a retransmission request for the X-ray image is received from the functional unit after the X-ray image is transferred to the functional unit;
a first setting step, in which the control unit sets, as the retransmission time, a period until a start of capturing of a next X-ray image after the transfer, when a moving image mode for capturing a plurality of X-ray images by continuously capturing X-ray images is set; and
a second setting step, in which the control unit sets a predetermined time as the retransmission time when a still image mode for capturing one X-ray image is set.

16. A method of controlling a radiation imaging apparatus including a radiation detector which obtains an image signal by detecting radiation, the method comprising:
an output step of outputting radiation image data based on the image signal to an external device;
a control step of starting in the output step re-outputting at least part of the radiation image data in accordance with a first signal from an external device, and receiving a second signal from the external device or continuing the re-outputting until elapse of a specific time from a start of the re-outputting; and
a setting step of setting the specific time based on selection of a second imaging mode executed sequentially after a first imaging mode of radiation imaging for obtaining the image signal.

17. A method of controlling a control device, the method comprising:
a reception step of receiving image data from a radiation detector;
a transmission step of transmitting, to the radiation detector, a signal for requesting retransmission of the image data and a signal indicating a retransmission time for interrupting retransmission of the image data before completion of the retransmission; and
a setting step of setting the retransmission time based on selection of a first imaging mode of radiation imaging for obtaining the image data and a second imaging mode executed sequentially after the first imaging mode.

18. The device according to claim 14, wherein the first imaging mode is moving image capturing and the second imaging mode is still image capturing.

* * * * *